US00PP37165P2

(12) United States Plant Patent
Ranney et al.

(10) Patent No.: US PP37,165 P2
(45) Date of Patent: Dec. 23, 2025

(54) ***BERBERIS* PLANT NAMED 'NCBT4'**

(50) Latin Name: *Berberis thunbergii*
Varietal Denomination: NCBT4

(71) Applicant: North Carolina State University, Raleigh, NC (US)

(72) Inventors: Thomas Green Ranney, Arden, NC (US); Andra Windorf Nus, Arden, NC (US); Irene Palmer, Arden, NC (US); John Tyler Nix, Arden, NC (US); Nathan Lynch, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 19/245,279

(22) Filed: Jun. 21, 2025

(51) Int. Cl.
*A01H 5/00* (2018.01)
*A01H 6/00* (2018.01)

(52) U.S. Cl.
USPC ..... Plt./241
CPC ..... *A01H 6/00* (2018.05)

(58) Field of Classification Search
USPC ..... Plt./241
CPC ..... A01H 5/00
See application file for complete search history.

*Primary Examiner* — Kent L Bell

(57) ABSTRACT

A new and distinct cultivar of *Berberis* plant named 'NCBT4' is disclosed, characterized by fiery red foliage color, a compact, rounded habit, and vigorous growth. The new cultivar is a *Berberis*, normally used for outdoor ornamental purposes.

2 Drawing Sheets

Latin name of the genus and species: *Berberis thunbergii.*
Cultivar denomination: 'NCBT4'.

BACKGROUND OF THE INVENTION

The new *Berberis* cultivar is a product of a planned breeding program conducted by the inventors to develop cultivars with new foliage colors and forms. The seed parent was the unpatented *Berberis thunbergii* 'H2007-001-033', of the inventors' breeding line. The pollen parent was *Berberis thunbergii* 'NCBT2' U.S. Plant Pat. No. 33,272. The cross resulting in this new cultivar was made during Spring 2011. The new cultivar was identified as a potentially interesting selection in the Summer of 2012, at a research nursery in Mills River, North Carolina.

Asexual propagation of the new cultivar 'NCBT4' by stem cuttings was first performed during the Summer of 2014 at a research nursery in Mills River, North Carolina. Subsequent propagation has shown that the unique features of this cultivar are stable and reproduced true to type in three successive propagation cycles.

Plants of the new cultivar were first shown to third parties Jun. 25, 2024, in the United States. Plants were shown at an invitational event in Grand Haven, MI. This disclosure was made directly by the inventor or one who obtained the claimed invention directly or indirectly from the inventor. This and all public disclosures made between Jun. 25, 2024, and the filing of this application fall within the exception allowed under 102(b)(1).

SUMMARY OF THE INVENTION

The cultivar 'NCBT4' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'NCBT4'. These characteristics in combination distinguish 'NCBT4' as a new and distinct *Berberis* cultivar:

1. Fiery red foliage color.
2. Compact, rounded habit.
3. Moderate mature size (3-5' tall by 3-4' wide).
4. Vigorous growth and rooting.

PARENT COMPARISONS

Plants of the new cultivar *Berberis* 'NCBT4' could not be compared to plants of the seed parent due to insufficient data.

Plants of the new cultivar *Berberis* 'NCBT4' are similar to plants of the pollen parent in most horticultural characteristics; however, plants of the new cultivar 'NCBT4' differ in the following:

1. Plants of the new cultivar are larger at maturity than plants of the pollen parent.

COMMERCIAL COMPARISONS

Plants of the new cultivar 'NCBT4' are comparable to plants of the commercial cultivar *Berberis thunbergii* 'Orange Rocket', U.S. Plant Pat. No. 18,411. The two *Berberis* cultivars are similar in most horticultural characteristics, however, the new cultivar 'NCBT4' differs in the following:

1. Plants of the new cultivar have a more rounded, mounded habit, while plants of this comparator have a more upright, columnar habit.
2. Young and mature foliage color of the new cultivar is fiery red, while the young foliage color of this comparator is red-orange, matures to green, returning to ruby red in autumn.

Plants of the new cultivar 'NCBT4' are comparable to the commercial cultivar *Berberis thunbergii* 'NCBT3', U.S.

Plant Pat. No. 35,050. The two *Berberis* cultivars are similar in most horticultural characteristics, however, the new cultivar 'NCBT4' differs in the following:

1. Plants of the new cultivar have a more rounded, mounded habit, while plants of this comparator have a more upright, columnar habit.

BRIEF DESCRIPTION OF THE PHOTOGRAPHS

This new *Berberis* is illustrated by the accompanying photographs which show the plant's form and foliage. The colors shown are as true as can be reasonably obtained by conventional photographic procedures. Colors in the photographs may differ slightly from the color values cited in the detailed botanical description, which accurately describe the colors of the new *Berberis*.

DETAILED BOTANICAL DESCRIPTION

Figure 1:
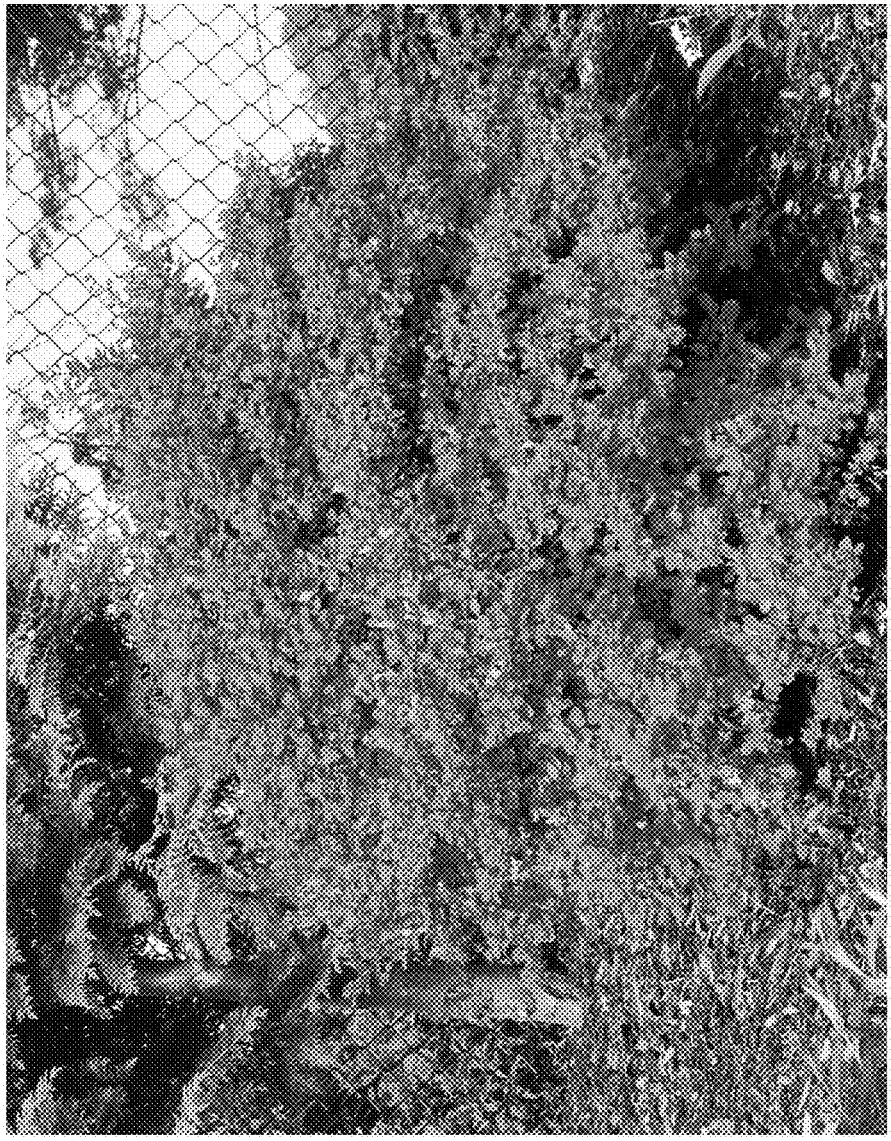
FIG. 1 is a color photograph showing the habit of a field-grown plant 'NCBT4' in summer 2024 in Mills River, North Carolina. This plant is approximately 7 years old.
Figure 2:
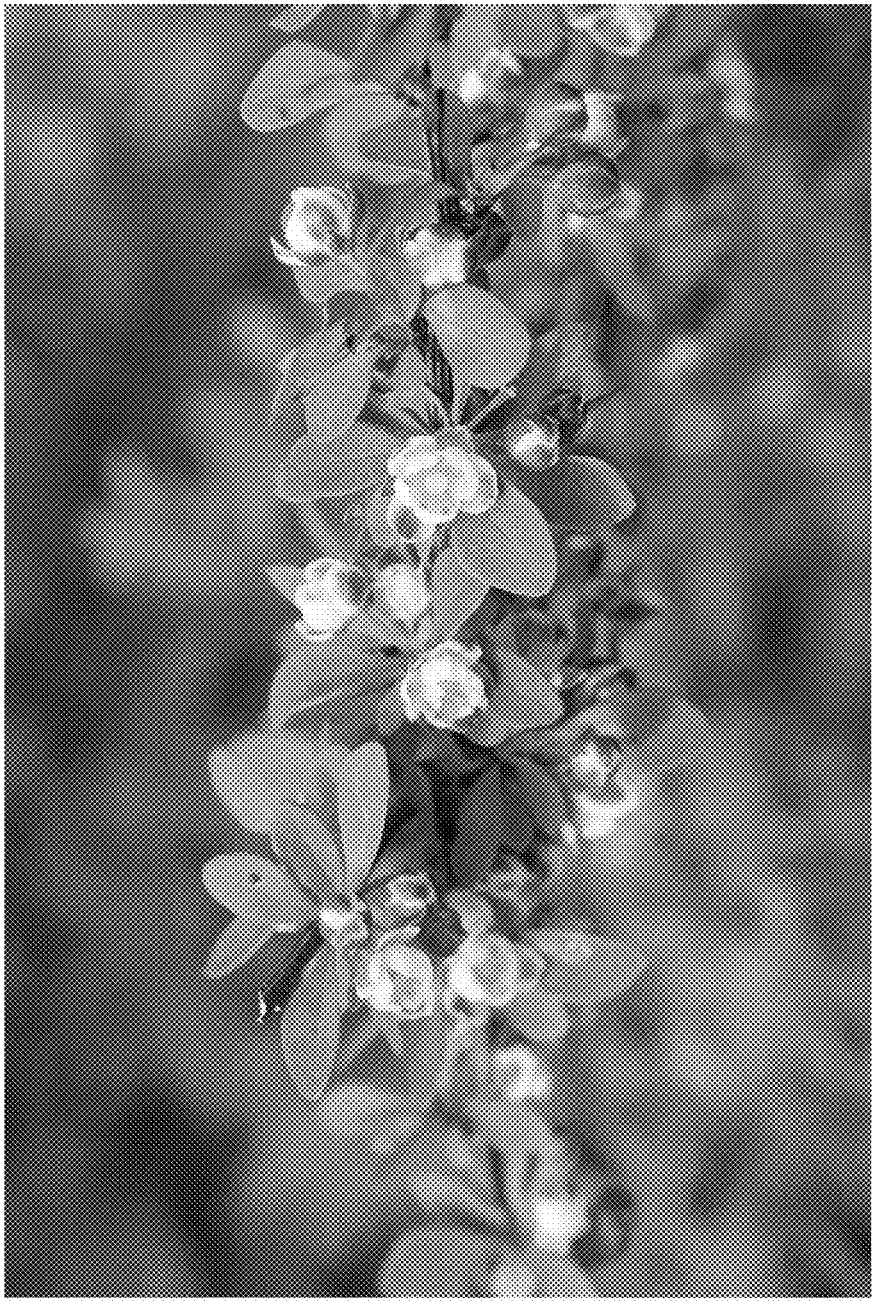
FIG. 2 is a color photograph showing a close-up view of the foliage and flowers of 'NCBT4' in summer 2024 in Mills River, North Carolina.

The following is a detailed description of the botanical characteristics of the new and distinct *Berberis* cultivar known by the denomination 'NCBT4'. The detailed description was taken on a seven-year-old field-grown plant in 2022 in Mills River, North Carolina. All colors cited herein refer to The Royal Horticultural Society Colour Chart (The Royal Horticultural Society (R.H.S.), London, 2015, Sixth Edition). Where specific dimensions, sizes, colors, and other characteristics are given, it is to be understood that such characteristics are approximations or averages set forth as accurately as practicable.

Botanical classification: *Berberis thunbergii* 'NCBT4'.

PROPAGATION

Type of propagation typically used: Softwood cuttings.

Root description: Very thin, fibrous, not fleshy, freely branching. New roots colored near RHS Yellow-White 158D. Older roots colored near Grey-Brown 199D.

PLANT

Age of plant described: 7 years.

Plant type: Flowering shrub.

Growth habit: Densely branched and rounded.

Plant spread: 100 to 120 cm.

Plant height: 100 to 120 cm.

Stems, shoots, branches:

- *Shoots* (*current year's growth*).—Shoot length: Average 9.6 cm (range 7.0 to 13.0 cm). Shoot diameter: About 0.2 cm. Color: RHS Greyed-Orange 166A. Texture: Glabrous.
- *Shoots* (*prior year's growth*).—Stem length: About 10 cm. Stem diameter: About 0.2 cm. Color: RHS Brown 200A. Texture: Glabrous.
- *Branches* (*woody branches* 2-4 *years old*).—Branch length: About 20 cm. Branch diameter: Average 0.8 cm (0.3 to 1.2 cm). Color: RHS Brown N200B. Texture: Glabrous.

Internode length: Average 3.7 cm (1.2 to 7.2 cm).

FOLIAGE

Leaf:

- *Type*.—Simple.
- *Persistence*.—Deciduous.
- *Arrangement*.—Alternate, whorled.
- *Shape*.—Obovate to rounded.
- *Length of lamina*.—Average 1.7 cm (1.1 to 2.0 cm).
- *Width*.—Average 0.8 cm (0.4 to 1.3 cm).
- *Apex*.—Acute to obtuse.
- *Base*.—Attenuate.
- *Margin*.—Entire.
- *Color, exterior emerging foliage*.—Upper: RHS Red 46A. Lower: RHS Red 183D.
- *Color, interior emerging foliage*.—Upper: RHS Yellow-Green N144A. Lower: RHS Yellow-Green 151A.
- *Color, exterior mature foliage*.—Upper: RHS Red 185A. Lower: RHS Red 182B.
- *Color, interior mature foliage*.—Upper: Near RHS Yellow-Green N144C. Lower: Near RHS Yellow-Green 145B.
- *Texture*.—Glabrous all surfaces.
- *Venation*.—Pinnate.
- *Vein color, emerging foliage*.—RHS Red 46A.
- *Vein color, mature foliage*.—RHS Red 185A.
- *Leaf attachment*.—Petiolate.

Petiole:

- *Length*.—About 0.2 cm.
- *Diameter*.—About 0.1 cm.
- *Color*.—RHS Red 46A.
- *Texture*.—Glabrous.

Spines:

- *Number*.—1 per node.
- *Length*.—Average 0.6 cm (0.4 to 1 cm).
- *Width*.—Less than 0.1 cm.
- *Color*.—Near RHS Greyed-Red 179B.

FLOWER

Inflorescence:

- *Description*.—Umbellate fascicles occurring in the axis along the underside of branches.
- *Number of flowers per inflorescence*.—2 to 4.
- *Flowering season*.—Mid-April to May in Mills River, NC.
- *Diameter*.—Average 1.6 cm (1.5 to 1.8 cm).
- *Height*.—Average 1.3 cm (1.2 to 1.4 cm).

Flower:

- *Shape*.—Star-shaped.
- *Diameter*.—Average 0.9 cm (0.8 to 1.0 cm).
- *Height*.—Average 0.5 cm (0.4 to 0.5 cm).

Bud:

- *Shape*.—Rounded.
- *Length*.—About 0.4 cm.
- *Width*.—About 0.3 cm.
- *Color*.—RHS Red 46A.
- *Texture*.—Glabrous.

Petals:
*Number.*—5 to 6 petals.
*Arrangement.*—Whorled.
*Shape.*—Ovate.
*Length.*—About 0.3 cm.
*Width.*—About 0.2 cm.
*Margin.*—Entire.
*Apex.*—Obtuse.
*Base.*—Truncate.
*Color.*—Upper surface: RHS Yellow 7D. Lower surface: RHS Yellow 7D.
*Texture.*—Glabrous.

Sepals:
*Number.*—6 sepals.
*Arrangement.*—Whorled.
*Shape.*—Ovate.
*Length.*—About 0.2 to 0.4 cm.
*Width.*—About 0.1 to 0.3 cm.
*Margin.*—Entire.
*Apex.*—Acute.
*Base.*—Fused.
*Color.*—Upper: RHS Red 46A with Yellow 7D on edges. Lower: Mostly RHS Yellow 5D.
*Texture.*—Glabrous.

Peduncle:
*Length.*—Average 6.4 cm (3.2 to 9.5 cm).
*Diameter.*—Less than 0.1 cm.
*Color.*—RHS Red 46A.
*Texture.*—Glabrous.

REPRODUCTIVE ORGANS

Gynoecium:
*Pistil number.*—1.
*Pistil length.*—About 0.3 cm.
*Stigma shape.*—Rounded.
*Stigma color.*—RHS Yellow 7D.
*Style length.*—About 0.2 cm.
*Style color.*—RHS Yellow 7D.

Androecium:
*Stamen number.*—5.
*Filament length.*—About 0.1 cm.
*Filament color.*—RHS Orange-Yellow 22C.
*Anther shape.*—Globular.
*Anther length.*—Less than 0.1 cm.
*Anther color.*—RHS Orange-Yellow 22C.
*Amount of pollen.*—Moderate.
*Pollen color.*—RHS Yellow 8A.

FRUIT AND SEEDS

Fruit:
*Type.*—Drupe.
*Shape.*—Ovoid.
*Length.*—About 0.8 cm.
*Width.*—About 0.5 cm.
*Color.*—RHS Red 46B.
*Texture.*—Glabrous.

Seed:
*Number per fruit.*—1 to 2.
*Shape.*—Ovoid
*Length.*—About 0.6 cm.
*Width.*—About 0.3 cm.
*Color.*—RHS Brown 200B.
*Texture.*—Glabrous, shiny.

OTHER CHARACTERISTICS

Disease/pest resistance: 'NCBT4' is documented to be resistant to Wheat Rust (*Puccinia* spp.) (Federal Register, Department of Agriculture Animal and Plant Health Inspection Service, Docket No. APHIS-2023-0050). Neither resistance nor susceptibility to other diseases and pests of *Berberis* have been observed.

Cold hardiness: At least USDA zone 6b; testing has not been completed in colder zones.

What is claimed is:

1. A new and distinct cultivar of *Berberis* plant named 'NCBT4' as herein illustrated and described.

* * * * *